United States Patent
Bhai et al.

(10) Patent No.: US 11,800,993 B2
(45) Date of Patent: Oct. 31, 2023

(54) EXIT MONITORING SYSTEM FOR PATIENT SUPPORT APPARATUS

(71) Applicant: Hill-Rom Services, Inc., Batesville, IN (US)

(72) Inventors: Aziz Bhai, Fishers, IN (US); Dan R. Tallent, Hope, IN (US); Eugene Urrutia, Durham, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 509 days.

(21) Appl. No.: 16/913,158

(22) Filed: Jun. 26, 2020

(65) Prior Publication Data

US 2020/0405192 A1    Dec. 31, 2020

Related U.S. Application Data

(60) Provisional application No. 62/868,230, filed on Jun. 28, 2019.

(51) Int. Cl.
*A61B 5/11* (2006.01)
*A61B 5/00* (2006.01)

(52) U.S. Cl.
CPC .......... *A61B 5/1115* (2013.01); *A61B 5/1117* (2013.01); *A61B 5/1118* (2013.01); *A61B 5/7267* (2013.01); *A61B 5/7275* (2013.01); *A61B 5/746* (2013.01); *A61B 5/747* (2013.01); *A61B 2562/0252* (2013.01)

(58) Field of Classification Search
None
See application file for complete search history.

(56) References Cited

U.S. PATENT DOCUMENTS

| | | | |
|---|---|---|---|
| 7,746,218 B2 | 6/2010 | Collins, Jr. et al. | |
| 10,055,961 B1* | 8/2018 | Johnson | G06T 7/248 |
| 10,321,856 B2 | 6/2019 | Fu et al. | |
| 2006/0028350 A1* | 2/2006 | Bhai | A61B 5/1115 |
| | | | 177/144 |
| 2007/0132597 A1* | 6/2007 | Rodgers | G06Q 10/10 |
| | | | 348/E7.078 |
| 2009/0044334 A1* | 2/2009 | Parsell | A61G 7/0507 |
| | | | 5/424 |
| 2009/0119843 A1* | 5/2009 | Rodgers | G16Z 99/00 |
| | | | 705/3 |

(Continued)

FOREIGN PATENT DOCUMENTS

WO   2018080971 A1   5/2018

OTHER PUBLICATIONS

S. Bennett, Z. Ren, R. Goubran, K. Rockwood and F. Knoefel, "In-Bed Mobility Monitoring Using Pressure Sensors," in IEEE Transactions on Instrumentation and Measurement, vol. 64, No. 8, pp. 2110-2120, Aug. 2015, doi: 10.1109/TIM.2015.2426331. (Year: 2015).*

(Continued)

*Primary Examiner* — Benjamin S Melhus
(74) *Attorney, Agent, or Firm* — Merchant & Gould P.C.

(57) ABSTRACT

An exit prediction system receives movement data, divides the movement data into segments of time, extracts features from each segment of time, and determines a pattern of movement from the extracted features. A patient exit from a patient support apparatus is predicted based on the determined pattern of movement.

20 Claims, 13 Drawing Sheets

(56) References Cited

U.S. PATENT DOCUMENTS

| | | | |
|---|---|---|---|
| 2011/0068935 A1* | 3/2011 | Riley | A61B 5/1115 340/575 |
| 2012/0253142 A1* | 10/2012 | Meger | A61B 5/113 600/301 |
| 2013/0246088 A1 | 9/2013 | Huster et al. | |
| 2015/0025327 A1* | 1/2015 | Young | A61B 5/024 600/595 |
| 2015/0254956 A1* | 9/2015 | Shen | A61B 5/445 340/573.1 |
| 2015/0302310 A1* | 10/2015 | Wernevi | G16H 50/20 706/12 |
| 2016/0193095 A1* | 7/2016 | Roussy | A61G 7/0524 5/616 |
| 2016/0354044 A1* | 12/2016 | Young | A61B 5/746 |
| 2017/0055882 A1* | 3/2017 | Al-Ali | A61B 5/002 |
| 2017/0055917 A1* | 3/2017 | Stone | A61B 5/1115 |
| 2017/0155877 A1* | 6/2017 | Johnson | G06V 20/52 |
| 2017/0169691 A1* | 6/2017 | Kirenko | G08B 21/0446 |
| 2017/0224253 A1* | 8/2017 | Berlin | A61B 5/1115 |
| 2018/0008168 A1* | 1/2018 | Pearlman | A61B 5/002 |
| 2018/0146889 A1* | 5/2018 | Akatsu | A61B 5/1036 |
| 2019/0053707 A1 | 2/2019 | Lane et al. | |
| 2019/0214146 A1* | 7/2019 | Dunias | A61B 5/1117 |
| 2019/0336085 A1* | 11/2019 | Kayser | A61B 5/447 |
| 2020/0265950 A1* | 8/2020 | Hosoi | A61B 5/1118 |
| 2021/0007676 A1* | 1/2021 | Chronis | A61B 5/1115 |
| 2021/0035437 A1* | 2/2021 | Zhang | G08B 21/22 |
| 2021/0100492 A1* | 4/2021 | Knight | A61B 5/7264 |
| 2021/0210198 A1* | 7/2021 | Lin | G16H 40/67 |
| 2021/0345910 A1* | 11/2021 | Pearlman | G01L 1/26 |
| 2022/0071512 A1* | 3/2022 | McAnena | A61B 5/6844 |

OTHER PUBLICATIONS

B. Chwyl, A. G. Chung, M. J. Shafiee, Y. Fu and A. Wong, "DeepPredict: a deep predictive intelligence platform for patient monitoring," 2017 39th Annual International Conference of the IEEE Engineering in Medicine and Biology Society (EMBC), 2017, pp. 4309-4312, doi: 10.1109/EMBC.2017.8037809. (Year: 2017).*

T. -X. Chen, R. -S. Hsiao, C. -H. Kao, W. -H. Liao and D. -B. Lin, "Bed-exit prediction based on convolutional neural networks," 2017 International Conference on Applied System Innovation (ICASI), 2017, pp. 188-191, doi: 10.1109/ICASI.2017.7988382. (Year: 2017).*

M. Alaziz et al., "MotionTree: a Tree-Based In-Bed Body Motion Classification System Using Load-Cells," 2017 IEEE/ACM International Conference on Connected Health: Applications, Systems and Engineering Technologies (CHASE), 2017, pp. 127-136, doi: 10.1109/CHASE.2017.71 (Year: 2017).*

\* cited by examiner

EXIT MONITORING SYSTEM FOR PATIENT SUPPORT APPARATUS

BACKGROUND

Patients in care facilities, such as hospitals, clinics, nursing homes, and the like are often in compromised medical conditions. Injuries sustained by patients in care facilities result in significant healthcare costs. In an effort to prevent such injuries, various protocols are implemented to mitigate the risks. For example, patients who are at risk of falling when moving unassisted may be identified as fall risks, and certain systems may be implemented to reduce the opportunity for the patients to move about the room unassisted.

In some systems, a patient support apparatus such as a hospital bed includes sensors that collect data to generate an alarm when it is determined that a patient is likely to exit the bed. Some systems utilize fixed thresholds such that when the patient moves beyond a boundary, an alarm is triggered. Other systems generate alarms based on a detected center of gravity of the patient. However, these systems are not able to predict that a patient will exit the bed based on the movements of the patient such that these systems are unable to provide an early warning to caregivers. Also, the patient may go through different types of motions while in the bed that may trigger an alarm even though the patient is not likely to exit the bed. The false alarms and inability to provide an early warning contribute to patient falls, which result in increased costs, prolonged stays in care facilities, and delayed patient recovery.

SUMMARY

In one aspect, an exit prediction system comprises: at least one processor; and a memory storing instructions which, when executed by the at least one processor, cause the system to: receive movement data; divide the movement data into segments of time; extract features from each segment of time; determine a pattern of movement from the extracted features; and predict a patient exit from a patient support apparatus based on the determined pattern of movement.

In another aspect, a method of predicting patient exit from a patient support apparatus comprises: receiving motion profiles; pre-categorizing the motion profiles as non-exit motion or exit motion; extracting features from the pre-categorized motion profiles; generating a bed exit prediction model using the extracted features; and predicting patient exit from the patient support apparatus using the model.

In another aspect, a non-transitory computer readable storage media, including computer readable instructions which when read and executed by a computing device, cause the computing device to: receive motion profiles; pre-categorize the motion profiles as non-exit motion or exit motion; extract features from the pre-categorized motion profiles; generate a bed exit prediction model using the extracted features; and predict patient exit from the patient support apparatus using the model.

BRIEF DESCRIPTION OF THE DRAWINGS

The following drawing figures, which form a part of this application, are illustrative of the described technology and are not meant to limit the scope of the disclosure in any manner. The features illustrated in the drawings are not necessarily drawn to scale.

DETAILED DESCRIPTION

Figure 1:
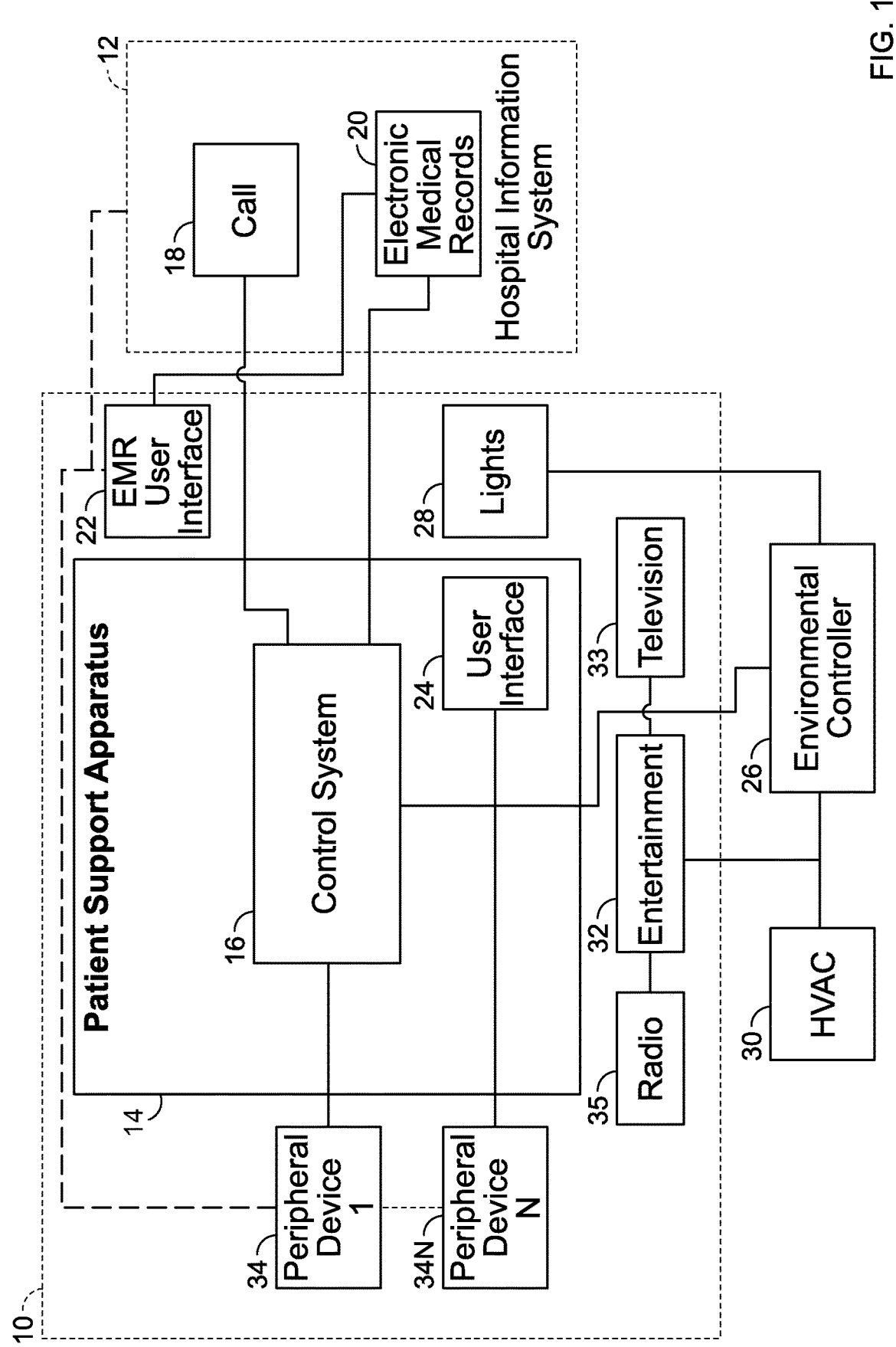
FIG. 1 is a schematic diagram of a patient support apparatus and a hospital information system.

Various embodiments and advantages are explained more fully with reference to the non-limiting embodiments that are described and illustrated in the accompanying drawings and detailed in the following description. The features of one embodiment may be employed with other embodiments, even if not explicitly stated herein. The embodiments provided herein are illustrative and should not be construed as limiting the scope of the claimed subject matter, which is defined solely by the appended claims. Also, like reference numerals may represent similar parts throughout the several views of the drawings.

The present disclosure describes improved systems and methods for estimating a likelihood of a patient exit from a patient support apparatus. The systems and methods assist caregivers in preventing unadvised, unmonitored patient exits and thus help prevent patient falls. The systems and methods allow for different patients to be monitored with varying levels of scrutiny, based at least in part on the needs of the individual patients, and facilitate efficient and effective monitoring of multiple patients by a remote caregiver.

The systems and methods described herein process data from specialized devices and sensors such as load cells that are included in a patient support apparatus. The data includes patient movement data that is processed to estimate a patient exit from the patient support apparatus. The systems and methods described herein more efficiently process the patient movement data. Further, the patient movement data is used in a practical application which is to provide an estimate of a patient exit from the patient support apparatus. In certain embodiments, the systems and methods are programmed to use the patient movement data to calculate a score indicating the likelihood of a patient exit from the patient support apparatus, and the score is presented to a caregiver to alert the caregiver of a possible patient exit to provide an early warning and mitigate the impact of such patient exit.

FIG. 1 is a schematic diagram of a patient support apparatus 14 and a hospital information system 12, according to one embodiment. The patient support apparatus 14 is positioned in a room 10 of a patient care facility. This exemplary embodiment is provided herein as one example of an environment in which a patient support apparatus 14 may be positioned and used. It is not intended to be limiting.

In some example embodiments, the patient support apparatus 14 referenced below will be referred to below as a "bed" such as a hospital bed. In alternative embodiments, the patient support apparatus 14 may be a chair, a recliner, or any other apparatus that supports a patient. The patient support apparatus 14 may be located in a patient care facility such as a hospital, clinic, nursing home, and the like, or in a patient's home.

The hospital information system 12 includes a caregiver call system 18 and an electronic medical records system 20. Both the caregiver call system 18 and electronic medical records system 20 store patient information. For example, the patient information is stored in one or more memories of the caregiver call system 18 and electronic medical records system 20, and is continuously updated. In certain embodiments, the caregiver call system 18 and electronic medical records system 20 receive the patient information directly from a control system 16 of the patient support apparatus 14.

The electronic medical records system 20 is accessible by a caregiver via an EMR user interface 22 to input patient information and enter orders while the caregiver is in the room 10. The electronic medical records system 20 can communicate with the EMR user interface 22 through a network such as the network 250 shown in FIG. 2. The EMR user interface 22 may be provided on a computing device used by the caregiver. Additional user interfaces may also be included throughout the patient care facility to interface with the hospital information system 12, and the electronic medical records system 20.

In certain embodiments, the control system 16 includes a user interface 24 that can be used by the patient supported on the patient support apparatus 14 or a caregiver in the room 10 to provide inputs to the control system 16 or display outputs from the control system 16. The control system 16 communicates with the caregiver call system 18 and electronic medical records system 20 through a network such as the network 250 shown in FIG. 2.

In one example, the user interface 24 is positioned on the patient support apparatus 14 and may be used by the caregiver to access the electronic medical records system 20 through the control system 16. In a further example, the patient support apparatus 14 is in communication with the electronic medical records system 20 via the control system 16, and acts as a peripheral device to the electronic medical records system 20.

The control system 16 further communicates with an environmental systems controller 26 which provides an interface between the patient support apparatus 14 and various environmental systems in the room 10 including lights 28, heating-ventilating-air-conditioning (HVAC) system 30, and entertainment devices 32 such as a television 33 or radio 35. The environmental systems controller 26 provides information to the control system 16 and acts on instructions from the control system 16 to modify operation of the various environmental systems in the room 10. The information from the environmental systems controller 26 is stored in memory associated with the environmental systems controller 26, and is updated as parameters of the environmental systems in the room 10 change.

The control system 16 is also in communication with one or more peripheral devices 34 positioned in the room 10. The peripheral devices 34 may each perform a therapeutic or diagnostic function. For example, the peripheral device 34 can include a ventilator, heart monitor, blood pressure monitor, infusion device, blood oxygen monitor, sequential compression device, high-frequency chest wall oscillation device, and the like.

In one example, at least one of the peripheral devices 34 is a patient monitoring device. In this example, one or more wireless and/or wired sensors are associated with the patient, and vital signs data from those sensors are communicated to the patient monitoring device. The data can be processed by the patient monitoring device and communicated to the caregiver call system 18 and electronic medical records system 20.

The control system 16 may utilize information stored in a memory associated with a peripheral device 34. For example, diagnostic values such as a heart rate, blood pressure, or other diagnostic values may be stored in a memory device of a peripheral device 34, and acquired by the control system 16. In certain examples, the peripheral devices 34 may communicate to the control system 16 via a wireless network connection, or a network connection such as a controller area network (CAN) such that the information stored on the peripheral device 34 is accessible by the control system 16. In some further examples, the control system 16 utilizes information stored in a memory device of the hospital information system 12 including in the caregiver call system 18 and electronic medical records system 20. In other examples, the information is stored in a memory device of the control system 16.

As illustrated in FIG. 1, any number of peripheral devices 34 may be in communication with the patient support apparatus 14. It should be understood that the peripheral devices 34 may also be in direct communication with the hospital information system 12 without being connected through the patient support apparatus 14.

The caregiver call system 18 generates alarms to notify caregivers of conditions based on signals from the control system 16 and information from the peripheral devices 34 and electronic medical records system 20. The caregiver call system 18 also provides a communication link, such as audio or video communications, between a patient supported on the patient support apparatus 14 and a caregiver positioned at a remote location.

For example, the caregiver call system 18 can include communication badges, that include telephone or other voice communication capability, that are worn by caregivers to facilitate direct communication between caregivers and the patient positioned on the patient support apparatus 14. In this way, the caregiver call system 18 acts as a dispatch system to provide instructions to caregivers when various conditions warrant the intervention of the caregiver either to adjust equipment or respond to the needs of a particular patient.

Figure 2:
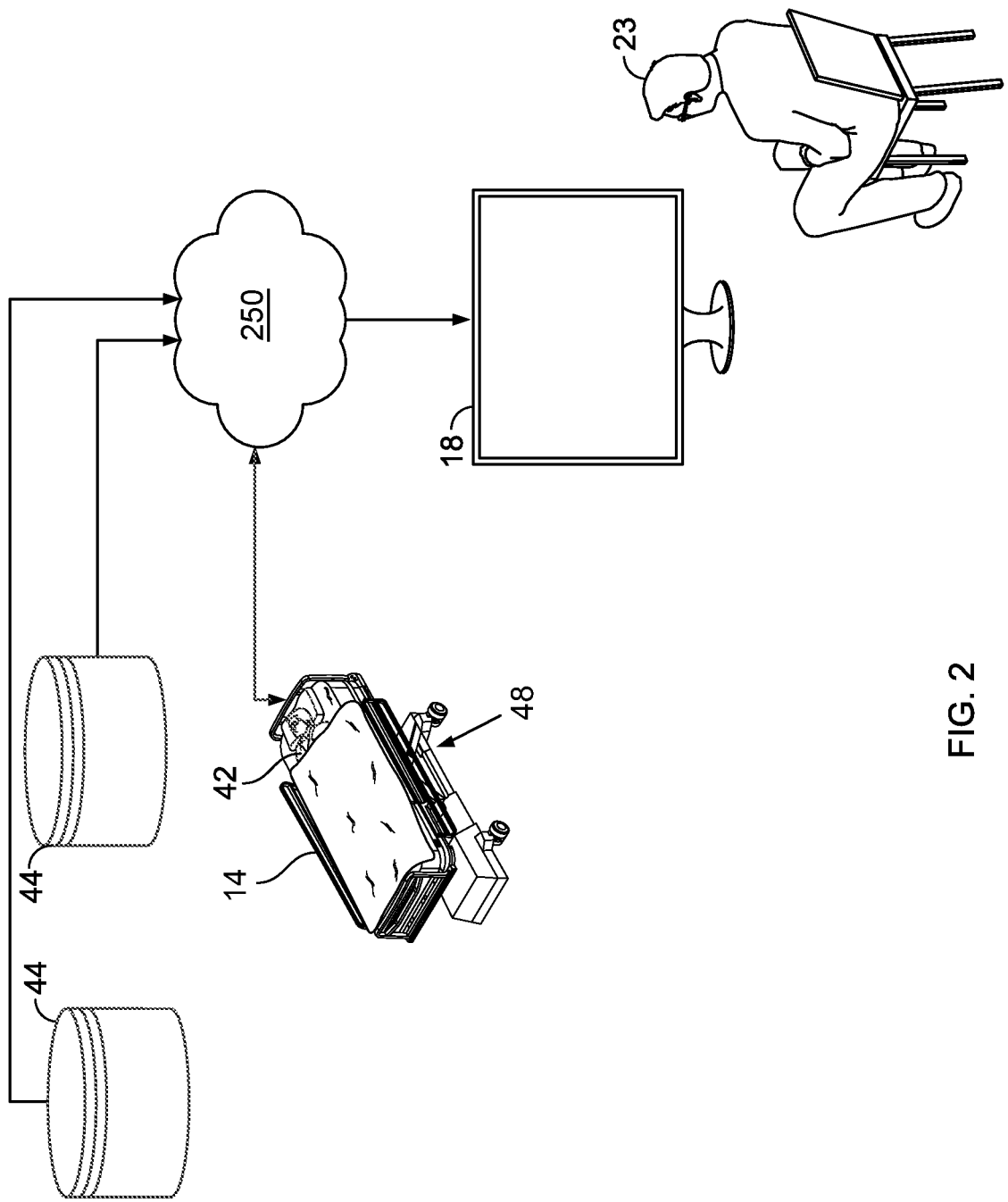
FIG. 2 is a schematic diagram of additional aspects of the patient support apparatus and hospital information system.

FIG. 2 is a schematic diagram of additional aspects of the patient support apparatus 14. In this example, a patient 42 lies on the patient support apparatus 14 which is depicted as a hospital bed. The caregiver 23 and caregiver call system 18 are located remotely from the patient 42 such that they are located in another area of the patient care facility.

The patient support apparatus 14 includes a plurality of load cells 48 to detect movements of the patient 42 on the patient support apparatus 14. The load cells 48 generate an electrical signal whose magnitude is proportional to the force being measured. In certain embodiments, the load cells 48 are hydraulic, pneumatic, or strain gauge load cells. In one example, the load cells 48 are positioned under a mattress of the patient support apparatus 14 and include at least four load cells such as loads cell under the right and left upper body portions and right and left lower body portions of the mattress.

One or more databases 44 store data collected from the patient support apparatus 14 including the load cells 48. The databases 44 may also store data from the hospital information system 12 including the electronic medical records system 20. The databases 44 are accessible by the caregiver call system 18 through the network 250.

Figure 3:
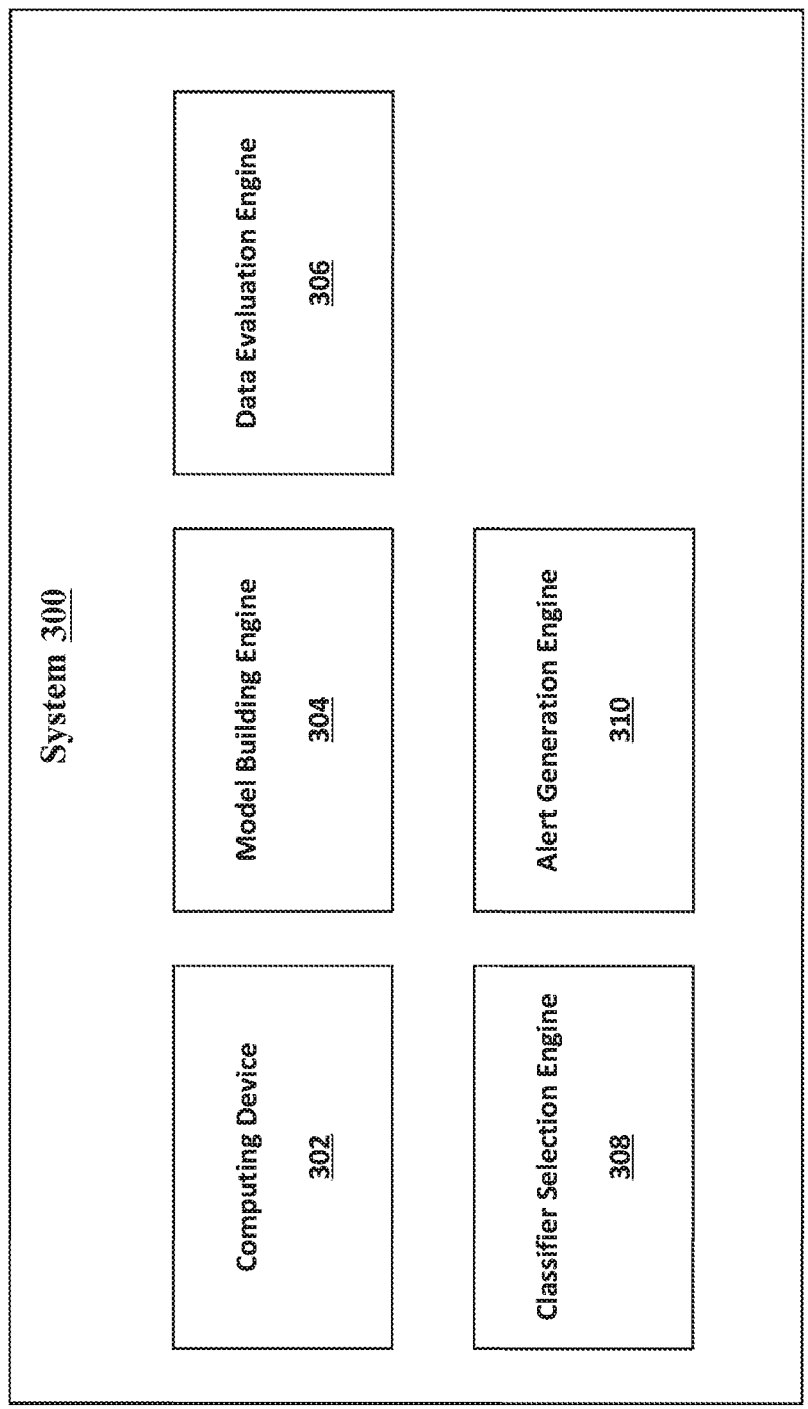
FIG. 3 is a schematic block diagram of a system that estimates a likelihood of a patient exiting the patient support apparatus.

FIG. 3 is a schematic block diagram of a system 300 that estimates a likelihood of a patient exiting the patient support apparatus 14. In certain embodiments, the system 300 is a part of the caregiver call system 18, or at least communicates with the caregiver call system 18. In alternative embodiments, the system 300 is a part of the patient support apparatus 14, peripheral devices 34, or electronic medical records system 20, or is a server or cloud-based computing platform. In a general sense, the system 300 estimates a likelihood of an exit from the patient support apparatus 14 for a given patient. The estimated likelihood of exit can be used, as described herein, to mitigate falls through alerting and other actions. The system 300 includes one or more computing devices 302, a model building engine 304, a data evaluation engine 306, a classifier selection engine 308, and an alert generation engine 310.

The one or more computing devices 302 process the data from the databases 44, and communicate with the model building engine 304, data evaluation engine 306, classifier selection engine 308, and alert generation engine 310. The computing devices 302 include at least one processor that executes instructions stored in a memory device to implement one or more of the methods described herein. An example of a computing device 302 as used herein is described in more detail with respect to at least FIG. 12.

The model building engine 304 operates to build a bed exit prediction model that is used to evaluate and classify the movements by the patient 42 on the patient support apparatus 14. The model building engine 304 uses one or more machine learning techniques to build the bed exit prediction model. Example methods performed by some embodiments of the model building engine 304 are illustrated and described with respect to FIGS. 6 and 7.

The data evaluation engine 306 operates to evaluate the data from the databases 44 to determine whether the data indicates that the patient 42 is likely or unlikely to exit to the patient support apparatus 14. In some embodiments, the data evaluation engine 306 uses the bed exit prediction model generated by the model building engine 304.

In certain embodiments, the data evaluation engine 306 generates scores that quantify an estimated likelihood that the patient 42 will exit the patient support apparatus 14. The scores are updated on a periodic basis. This can be near-real-time, such as once per second, or based upon a greater period, such as once every five seconds, once a minute, etc. The scores can be compared to a threshold value. The threshold value can be specific to the patient (e.g., based upon the patient's prior history) or can be general to a population associated with the patient (e.g., age, sex, etc.). If a score exceeds a threshold, the caregiver 23 is alerted regarding a likelihood of the patient 42 exiting the patient support apparatus 14. The data evaluation engine 306 is described in more detail with respect to at least FIG. 9.

The classifier selection engine 308 operates to assign a classifier to the data from the databases 44 that indicates an estimated likelihood that the patient 42 will exit the patient support apparatus 14. In at least some embodiments, the classifier selection engine 308 filters the data from the databases 44 based on one or more characteristics including but not limited to a score generated by the data evaluation engine 306. The classifier selection engine 308 is described in more detail with respect to at least FIG. 10.

The alert generation engine 310 operates to generate one or more types of alerts to provide the caregiver 23 with a warning that the patient 42 is likely to exit the patient support apparatus 14. The alert generated by the alert generation engine 310 may be delivered in any suitable form, including audible, visual, and textual such as a text message, pager message, email, or other form of alert information, such as a message on a display device associated with the caregiver call system 18. Also, an alert can be provided to the patient 42 to stay in the bed, to be careful when exiting the bed, and the like. The alert provided to the patient 42 may be a voice command delivered over a microphone/intercom system in the room 10.

Figure 4:
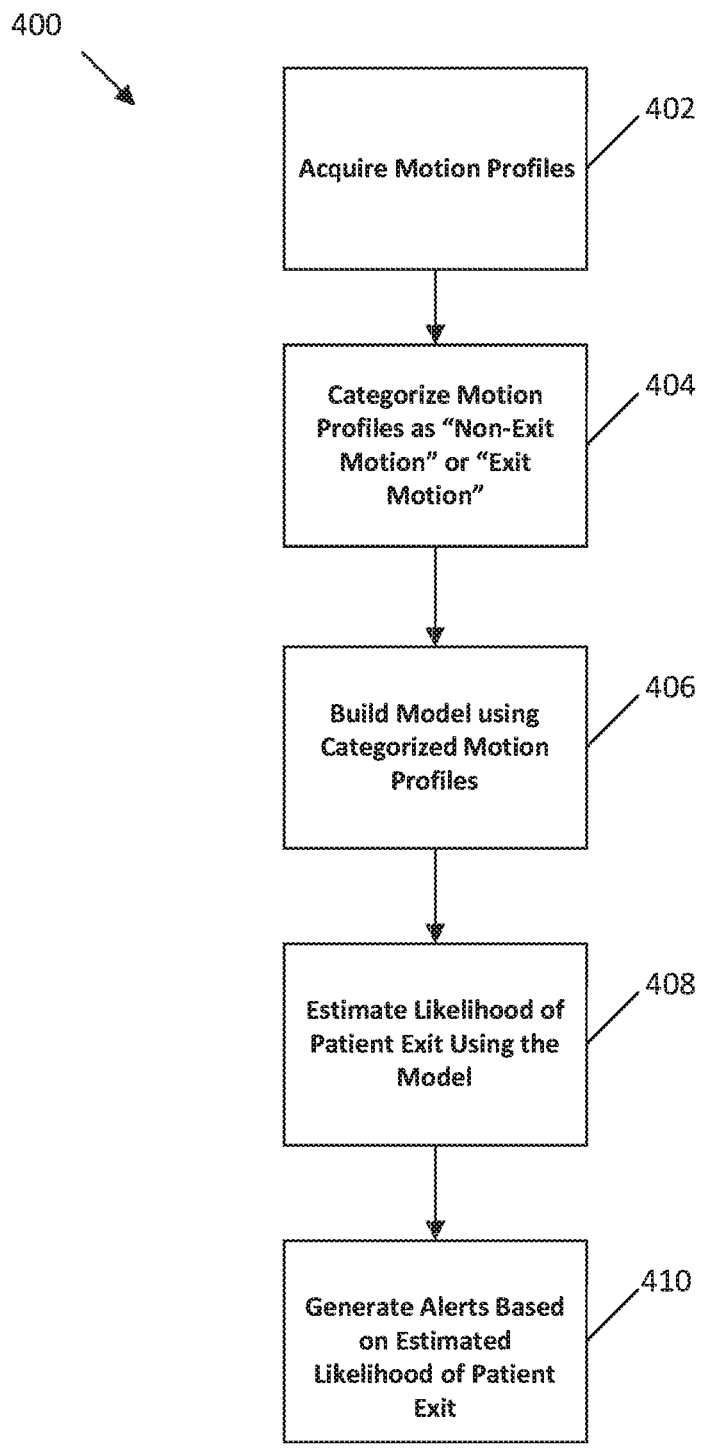
FIG. 4 illustrates a method of generating an alert based on an estimated a likelihood that a patient will exit the patient support apparatus.

FIG. 4 illustrates a method 400 of estimating a likelihood of a patient exit from the patient support apparatus 14. In certain examples, the method 400 is performed by the system 300 described above. The method 400 includes an operation 402 of acquiring motion profiles, an operation 404 of pre-categorizing the acquired motion profiles as a non-exit motion or an exit motion, an operation 406 of building a model using the pre-categorized motion profiles, an operation 408 of estimating a likelihood of patient exit using the model, and an operation 410 of generating an alert based on the estimated likelihood of patient exit.

At operation 402, motion profiles 500 (see FIG. 5) are acquired from the databases 44. As a patient spends time in the patient support apparatus 14, the patient will go through different types of motion profiles 500. Some illustrative examples include rolling to one side of patient support apparatus 14 to make themselves comfortable, sitting up while eating or during a visit by a doctor, or extending their body to reach for an object next to a side of the patient support apparatus 14. The motion profiles 500 are detected by the plurality of load cells 48, and are collected and transmitted by the control system 16 to at least one of the databases 44 via the network 250. In certain examples, the system 300 acquires the motion profiles 500 by accessing the databases 44 via the network 250.

Figure 5:
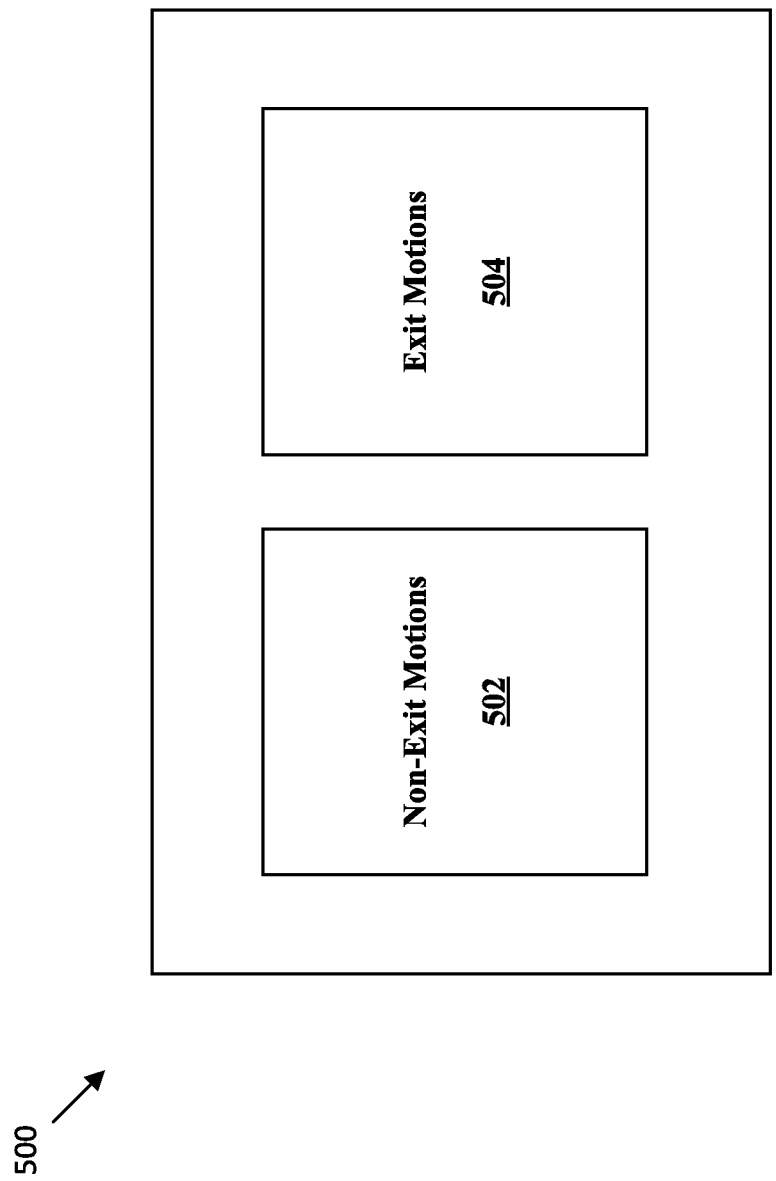
FIG. 5 is a schematic diagram of acquired motion profiles that are categorized as non-exit motions or exit motions.

At operation 404, the motion profiles 500 are pre-categorized as non-exit motions 502 or exit motions 504. FIG. 5 is a schematic diagram of the motion profiles 500 that are pre-categorized as non-exit motions 502 or exit motions 504.

Non-exit motions 502 are motion profiles that are typically done for patient comfort or are related to activities performed during routine examinations by a caregiver such as to avoid pressure ulcers. For example, while on the patient support apparatus 14, the patient may roll to the right or left side, reach out to the right or left side, roll around the center, or sit up. This list of examples is not exhaustive, and additional types of non-exit motions 502 are possible. Non-exit motions 502 do not generate an alert because they are not likely to result in an exit from the patient support apparatus 14.

Exit motions 504 are predictive of whether a patient will exit the patient support apparatus 14. While these motions may vary from patient to patient based on patient behavior and condition, an exit motion 504 can include exiting from the center to the right or left side of the patient support apparatus 14. For example, when a patient lays at the center of the patient support apparatus 14, the patient when attempting to exit will start from the center of the patient support apparatus and then move towards the right or left side. Thereafter, the patient will typically attempt to exit the patient support apparatus by extending their feet over the edge of the patient support apparatus before touching the ground with their feet.

Exit motions 504 may also include movements that start from the edge of the patient support apparatus 14. For example, in some instances, a patient may lay closer to the edge of the patient support apparatus 14 and thus the patient will attempt to exit the patient support apparatus starting from the edge.

Exit motions 504 may also include laying crosswise on the patient support apparatus 14 before starting to exit the patient support apparatus 14. For example, patients are sometimes positioned diagonally before they attempt to exit the patient support apparatus 14. Sometimes due to weakness, the patient 42 may grab the side rail of the patient support apparatus 14 to help them first roll closer to the edge of the patient support apparatus 14 before sitting-up to extend their feet over the edge. Thus, this may be another example of an exit motion 504. In addition to the above examples of exit motions 504, additional exit motions are possible such that the foregoing list of examples is not exhaustive.

At operation 406, a bed exit prediction model is built using the non-exit motions 502 and exit motions 504 that have been pre-categorized at operation 404. The model is built based on features extracted from the non-exit motions 502 and exit motions 504. In some embodiments, the model is built using one or more machine learning techniques. Further details of operation 406 are illustrated and described with respect to at least FIG. 6.

At operation 408, a likelihood of a patient exiting the patient support apparatus 14 is estimated using the model built at operation 406. In operation 408, uncategorized motion profiles are acquired, and subsequently entered into the model as inputs. The motion profiles can be continuously inputted into the model to continuously estimate a likelihood of a patient exit from the patient support apparatus 14. Alternatively, the uncategorized motion profiles 500 can be inputted based on the time of the day (e.g., during the nighttime), the location of the patient support apparatus 14 (e.g., whether in a supervised or unsupervised location), the location of the caregiver 23 (e.g., whether inside or outside the room 10), and the like.

In some embodiments, operation 408 includes using the bed exit prediction model to generate a score that quantifies the similarity of uncategorized motion profiles to pre-categorized exit motions 504. In some embodiments, the score is a numerical value in which higher values indicate uncategorized motion profiles that are more similar to pre-categorized exit motions 504, and in which lower values indicate uncategorized motion profiles that are less similar. In some embodiments, the scores are stored in a memory of the system 300.

At operation 410, an alert is generated based on the estimated likelihood of a patient exit from the patient support apparatus 14 determined from operation 408. Different alerts may be generated at operation 410 based on the score corresponding to how similar an uncategorized motion profile is to a pre-categorized exit motion 504. For example, an alert is delivered directly to the caregiver 23 when a higher score is generated. In contrast, an alert can be displayed on a display device associated with the caregiver call system 18 when a lower score is generated. Additional configurations are possible.

In addition to transmitting an alert to the caregiver 23, operation 410 can also include providing an alert to the patient 42. For example, the alert generated at operation 410 can include a voice command for the patient 42 to stay in the patient support apparatus 14, to be careful when exiting the patient support apparatus 14, and the like.

As described above, the alert generated at operation 410 may be delivered in any suitable form, including audible, visual, and textual such as a text message, pager message, email, or other form of alert information, such as a message on a display device associated with the caregiver call system 18. Also, the alert may include a classifier such as a numerical value, a color scheme, audible tones/strength, and the like to indicate the degree of patient exit likelihood (i.e., more likely vs. less likely) and whether the patient exit is imminent.

Figure 6:
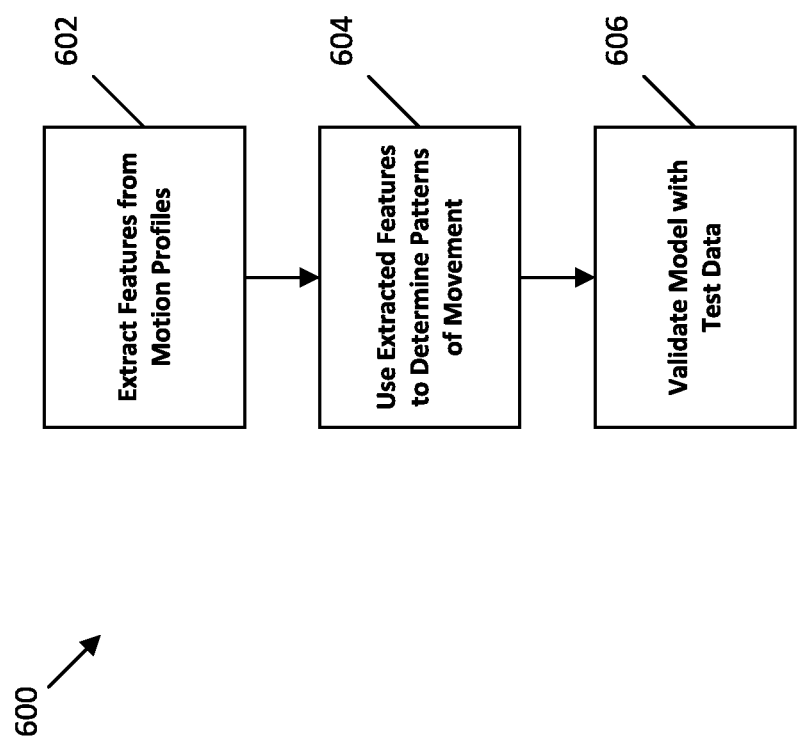
FIG. 6 illustrates a method of building a bed exit prediction model based on the acquired motion profiles.

FIG. 6 illustrates an example method 600 of building the bed exit prediction model based on the motion profiles 500 that is performed by some embodiments of the model building engine 304 (see FIG. 3) and that occurs in some embodiments at operation 406 of the method 400 (see FIG. 4). The bed exit prediction model can be used to classify uncategorized motion profiles 500 as non-exit motions 502 or exit motions 504.

The method 600 includes an operation 602 of extracting features from the motion profiles 500 that are pre-categorized as non-exit motions 502 or exit motions 504. The extracted features include both scalar and vector features.

Scalar features include the power spectral density of the load cells 48 such as the distribution of the load of the patient 42 over the load cells 48 on the patient support apparatus 14. The extracted scalar features can include the distribution ratios between the foot beams and upper body beams of the patient support apparatus 14. In some examples, the scalar features include the standard deviations of the distribution ratios.

Vector features include acceleration in the side-to-side, up-down, and diagonal directions on the patient support apparatus 14. Vector features may further include the change in the percentage of load distribution on each load cell 48 over time.

At operation 604, the features extracted from the motion profiles 500 are used to determine patterns in the non-exit motions 502 and exit motions 504 over time. Various types of pattern recognition techniques and classifiers can be used such as both classification and regression types. In some examples, the k-nearest neighbor algorithm (k-NN) is used. In one example, patterns of the load distribution on the load cells 48 during exit motions 504 are learned over time T. In certain examples the time T may vary depending on the behavior and condition of the patient including the speed at which the patient moves.

At operation 606, the bed exit prediction model is validated with test data. For example, the patterns determined at operation 604 are used by the model to evaluate the test data to objectively distinguish exit motions 504 from non-exit motions 502.

Figure 7:
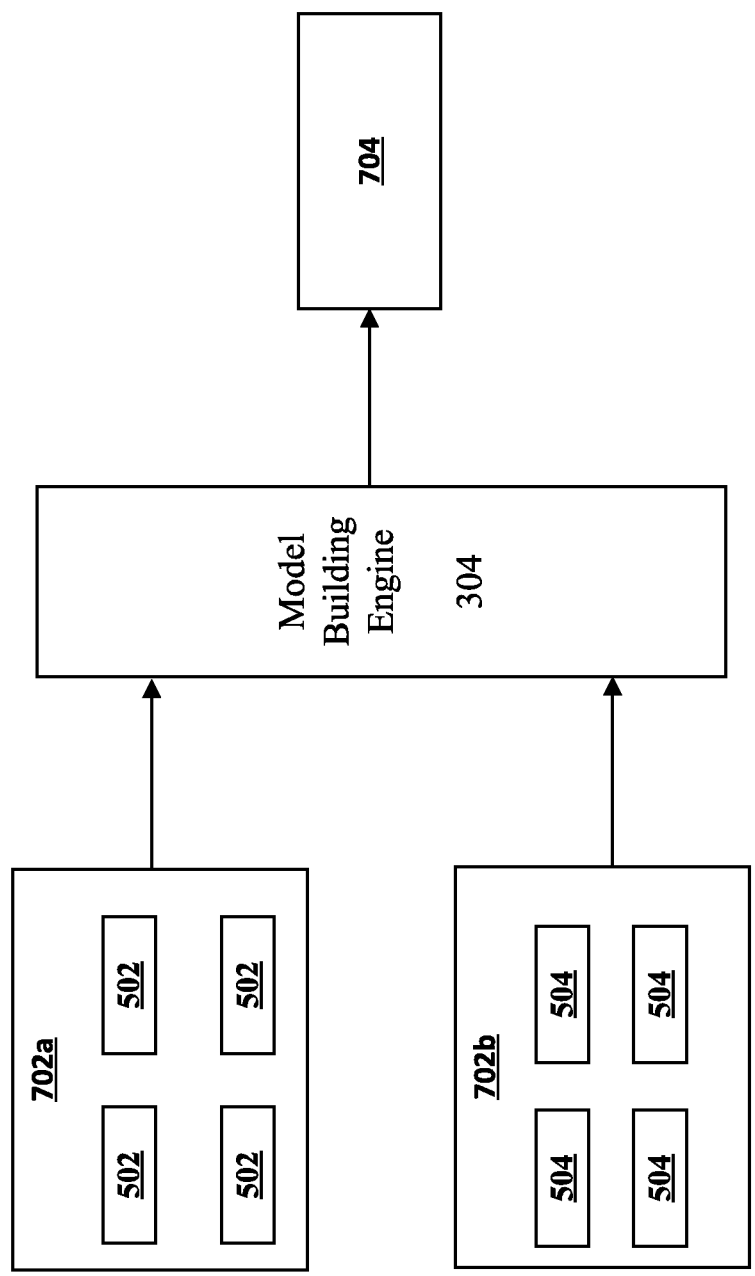
FIG. 7 is a schematic diagram of a model building engine.

FIG. 7 is a schematic diagram of the model building engine 304. The model building engine 304 receives a first set of inputs 702a which include motion profiles that are pre-categorized as non-exit motions 502 (see FIG. 5). The model building engine 304 also receives a second set of inputs 702b which include motion profiles that are pre-categorized as exit motions 504 (see FIG. 5). The first and second sets of inputs 702a, 702b are seed data used by the model building engine 304 to build a bed exit prediction model as an output 704.

In certain embodiments, the first and second sets of inputs 702a, 702b are assigned a speed classifier before they are inputted into the model building engine 304. For example, the first and second sets of inputs 702a, 702b can be assigned a fast speed classifier or a slow speed classifier such that the bed exit prediction model generated as output 704 can be calibrated for different patient motion speeds. Advantageously, this can overcome challenges where different patients move at different speeds such that one speed classifier would not satisfy all motion profiles 500 for all patients.

Multiple speed classifiers are used to calibrate the bed exit prediction model for various patient speeds. In certain embodiments, five different speed classifiers are used to calibrate the bed exit prediction model. As an illustrative example, a high speed classifier, a moderately high speed classifier, an intermediate speed classifier, a moderately low speed classifier, and a low speed classifier may be used.

The model building engine 304 uses machine learning to identify patterns from the first and second sets of inputs 702a, 702b to build the bed exit prediction model by distinguishing the exit motions 504 from the non-exit motions 502. In certain embodiments, the model building engine 304 uses deep learning or artificial intelligence to identify patterns from the first and second sets of inputs 702a, 702b to build the bed exit prediction model. As will be described in more detail, the bed exit prediction model is used by the data evaluation engine 306 to estimate a likelihood of the patient exiting the patient support apparatus 14.

Figure 8:
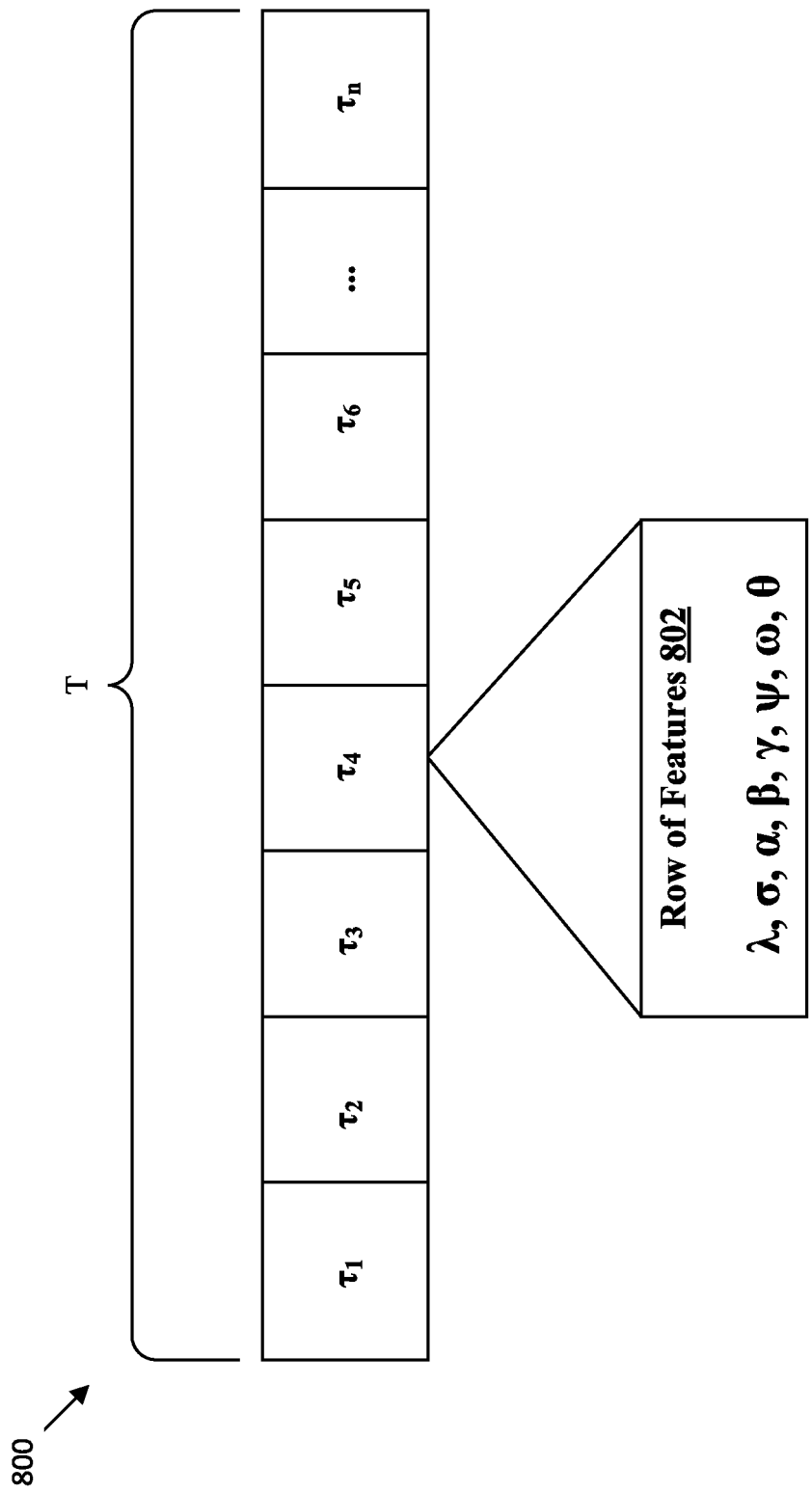
FIG. 8 schematically illustrates a machine learning logic used by the model building engine to identify patterns from the non-exit motions and exit motions.

FIG. 8 schematically illustrates a machine learning logic 800 that can be used by the model building engine 304 to identify the patterns from the motion profiles 500 including the non-exit motions 502 and exit motions 504. The machine learning logic 800 divides each motion profile 500 into segments of time $\tau_1 \ldots \tau_n$. In one example, each segment of time $\tau_1 \ldots \tau_n$ is one second. In other examples, each segment of time $\tau_1 \ldots \tau_n$ is less than one second to obtain a higher resolution for faster moving patients.

Each segment of time includes a row of features 802. Each row of features 802 includes one or more scalar and vector features, such as the ones described above. As an illustrative example, a percentage change in load λ detected by the load cells 48 is included in each row of features 802 for each of the segments of time $\tau_1 \ldots \tau_n$. Thus, the segments of time $\tau_1 \ldots \tau_n$ provide a pattern of the percentage change in load λ over time T. In one example, time T is about 5 seconds, and this period of time can be increased or decreased to help improve correlations between the non-exit motions 502 and exit motions 504, respectively.

The model building engine 304 learns from the rows of features 802 in each segment of time for each of the inputs that have identified as non-exit motions 502 or exit motions 504 to build the bed exit prediction model. Subsequently, the bed exit prediction model can be used to classify new motion profiles 500 that have not been pre-categorized as non-exit motions 502 or exit motions 504. For example, new motion profiles 500 are entered into the model and the rows of features 802 in each segment of time in the new motion profiles 500 are categorized by the model as a non-exit motion 502 or an exit motion 504.

Figure 9:
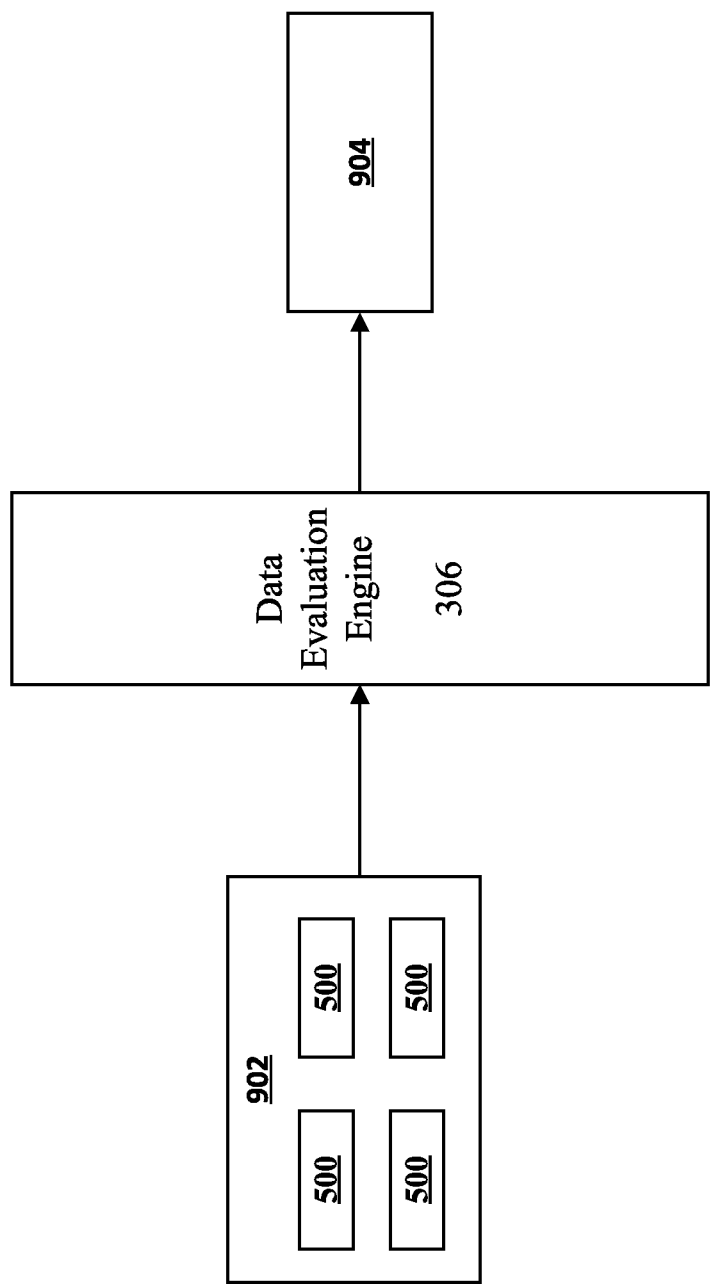
FIG. 9 is a schematic diagram of a data evaluation engine.

FIG. 9 is a schematic diagram of the data evaluation engine 306. The data evaluation engine 306 receives inputs 902, which are new motion profiles 500 that have not been categorized as non-exit motions 502 or exit motions 504. The inputs 902 are signals detected by the load cells 48 in the patient support apparatus 14. In certain embodiments, the inputs 902 are received by the system 300 from the databases 44. Alternatively, the system 300 can receive the inputs 902 directly from the control system 16 of the patient support apparatus 14. The data evaluation engine 306 uses the model from the model building engine 304 to produce outputs 904 that objectively estimate likelihood of a patient exit.

In some illustrative examples, the bed exit prediction model estimates a likelihood of patient exit based on whether a load distribution in the segments of time $\tau_1 \ldots \tau_n$ of a motion profile 500 changes according to a predetermined pattern. In further examples, the bed exit prediction model estimates a likelihood of patient exit based on whether the acceleration of the changes in the load distribution in the segments of time $\tau_1 \ldots \tau_n$ exceeds a predetermined threshold. For example, the acceleration of a patient during an exit motion 504 is typically greater than during a non-exit motion 502 because of the stop and start nature of the exit motion 504 as the patient exits the patient support apparatus 14 versus when they are not. The rows of features 802 of previous segments of time $\tau_1 \ldots \tau_n$ and future segments of time $\tau_1 \ldots \tau_n$ are learned by the model as the features of an exit motion 504.

As an illustrative example, a patient's movement is classified as an exit type when the load distribution changes in certain selected combinations or when the acceleration of the load distribution changes exceeds a certain threshold. Identification of an exit type motion triggers an alert. Additional types of conditions for triggering an alert are possible.

Figure 10:
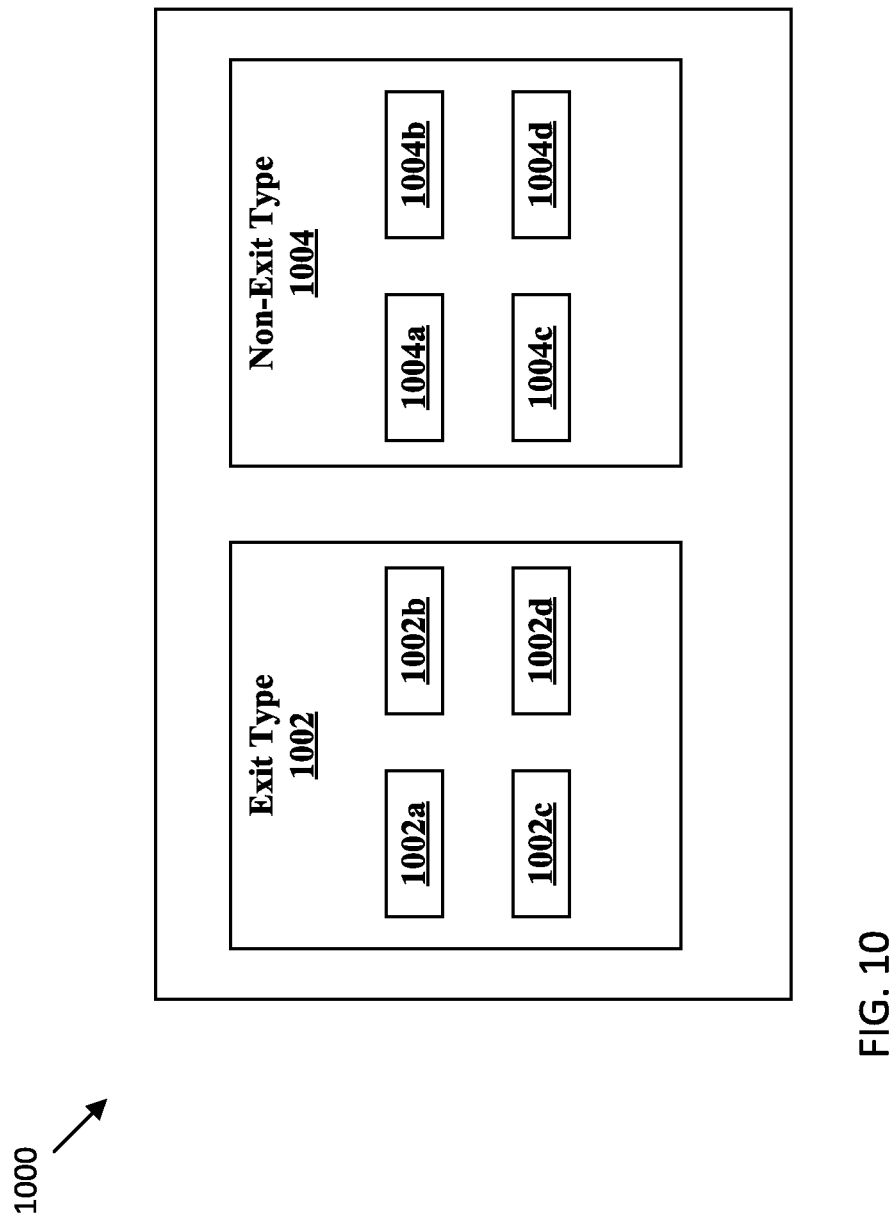
FIG. 10 schematically illustrates motion types and subclasses assigned by a classifier selection engine.

FIG. 10 schematically illustrates motion types and subclasses that are assigned by the classifier selection engine 308 for each segment of time during time T. In some embodiments, the classifier selection engine 308 assigns an output class 1000 for each segment of time $\tau_1 \ldots \tau_n$ based on the row of features 802. The output classes 1000 are assigned as either an exit motion type 1002 or a non-exit motion type 1004.

The exit motion type 1002 is indicative of a movement that will likely lead to a patient exit from the patient support apparatus 14. A non-exit motion type 1004 is indicative of a movement that will not likely lead to a patient exit from the patient support apparatus 14.

Additionally, the classifier selection engine 308 can further assign for each segment of time $\tau_1 \ldots \tau_n$ a subclass of the exit motion type 1002 or non-exit motion type 1004. For example, the exit motion type 1002 can include a subclass 1002a which indicates an exit motion type that it is less likely to be predictive of a patient exit because it has characteristic such as low acceleration. As another example, the non-exit motion type 1004 can include a subclass 1004a which indicates a non-exit motion type that may be predictive of a patient exit because it has characteristic such as high acceleration. Thus, the output classes and subclasses assigned for each segment of time $\tau_1 \ldots \tau_n$ based on the row of features 802 represents a decision corresponding to an exit or non-exit pattern in real-time.

The output classes 1000 and subclasses that are assigned to each segment of time over time T are monitored to provide real-time and continuous updates on whether a motion profile 500 is likely to lead to an exit from the patient support apparatus 14. Accordingly, higher granularity and predictive accuracy can be provided.

As an illustrative example, lower strength subclasses may be initially assigned based on rows of features 802 within a motion profile 500 such that the system 300 initially produces lower priority alerts, and subsequently higher strength subclasses may be assigned based on rows of features 802 within the motion profile 500 such that the system 300 escalates to produce higher priority alerts before an exit from the patient support apparatus 14 occurs. Advantageously, this can provide an early warning to caregivers to mitigate patient falls, while also reducing false alarms to mitigate alarm fatigue.

The real-time classification of segments within the motion profiles 500 can be presented to the caregiver 23 and/or used for alerting purposes. The classification of the segments of the motion profiles 500 provides a more accurate estimate of patient exit, thereby minimizing false alerts while still providing meaningful and optimized fall protection.

For example, systems that predict patient exit based on detecting a patient's center of gravity can generate false alarms when a patient rolls from left to right or from right to left even though this is normal in-bed motion because such systems will detect that the patient's body is no longer centered in the middle of the bed. The system 300 reduces and/or eliminates such false alarms by identifying patterns of movement from the extracted features to objectively distinguish between non-exit motions 502 and exit motions 504.

As another example, systems that predict patient exit based on detecting whether a portion of the patient's body has crossed a boundary can generate false alarms when a patient reaches out to the right or left side of the bed to grab an item next to the bed such as a cup of water even though the patient is not attempting to exit the bed. The system 300 reduces and/or eliminates such false alarms by identifying patterns of movement to objectively distinguish between non-exit motions 502 and exit motions 504.

Additionally, the bed exit prediction model can be calibrated for different patient speeds to further improve the predictive accuracy of the system 300 and further mitigate false alarms. As an illustrative example, the movement of a patient assigned to the patient support apparatus 14 can be monitored to determine which speed classifier should be used for calibrating the bed exit prediction model. In the example shown in FIG. 2, the movement of the patient 42 can be monitored by identifying changes in the loads detected from the load cells 48 over a predetermined period of time to assess the patient's speed. As an example, elderly or weak patients will move more slowly than young and healthy patients. The patient's speed can then be used to identify an appropriate speed classifier to calibrate the bed exit prediction model. As described above, multiple speed classifiers can be used to calibrate the bed exit prediction model for various patient motion speeds.

Figure 11:
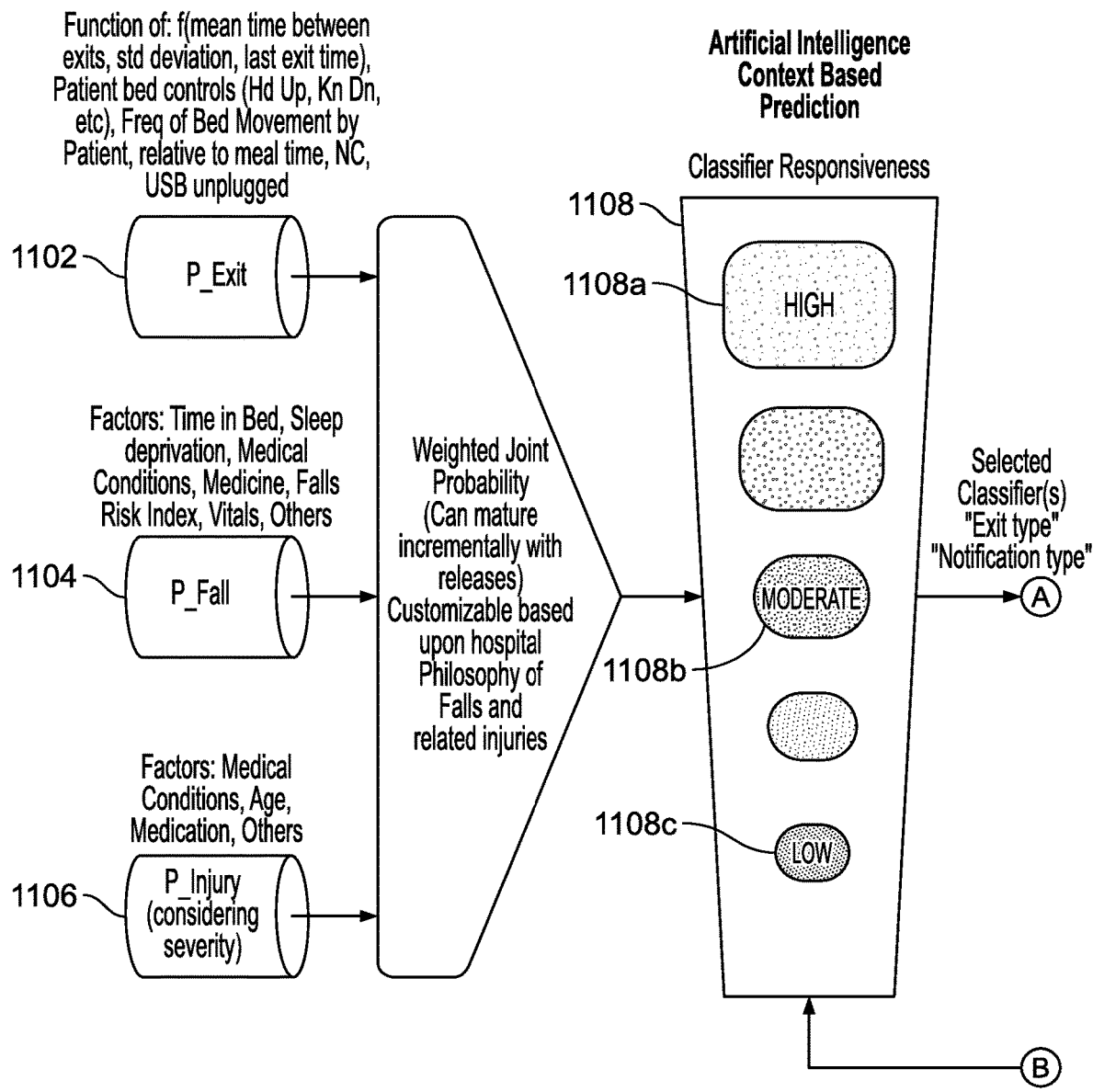
FIG. 11 schematically illustrates a context based system for estimating the likelihood of a patient exit.
Figure 11:
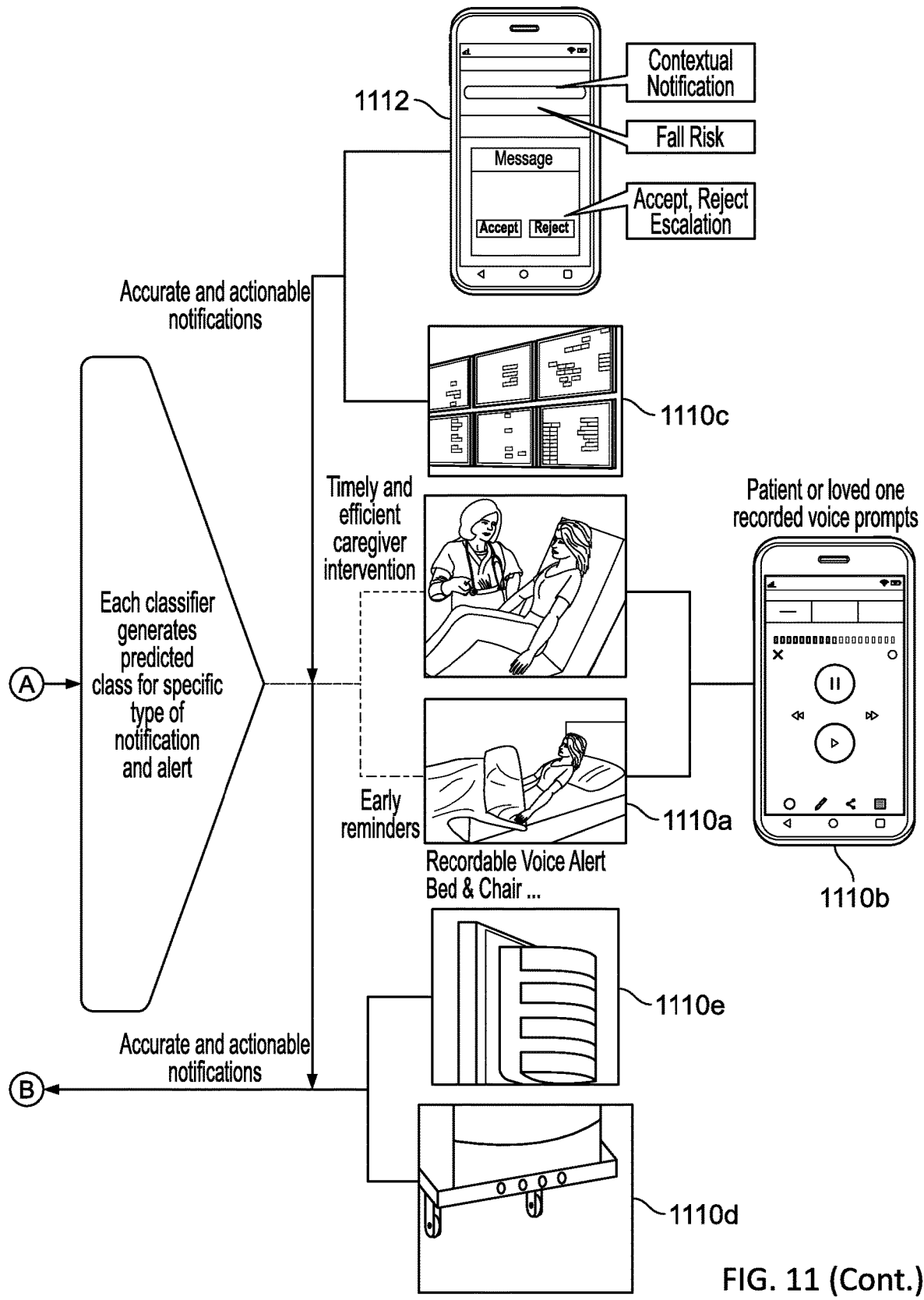

FIG. 11 schematically illustrates a system 1100 that furthers optimize the classification of the motion profiles 500 by estimating fall risks and injuries, and adjusting the sensitivity level for the bed exit prediction model. Additionally, the system 1100 optimizes response time priority between low priority notifications and high priority alerts by considering various factors that estimate the probability of a patient fall and resulting injuries after a patient exits the patient support apparatus 14 unattended.

Referring now to FIG. 11, additional sets of factors may be used to customize the sensitivity of the bed exit prediction model and the alert priority. Machine learning and/or artificial intelligence are used to optimize response time between low and high priority alerts determined from factors relevant to patient exit, fall, and injury probability. Multiple possible response times can be selected such that caregivers can prioritize their workflow.

As shown in FIG. 11, a first set of factors 1102 may further improve the accuracy of bed exit prediction. For example, the first set of factors 1102 may include data such as mean time between exits, time of last exit, sleep cycles of the patient, mean time between bladder/bowel movements, current position of the hospital bed, state of the bed side rails, patient activity level on the patient support apparatus, time of day, meal time, and the like.

A second set of factors 1104 can be used to predict whether a patient fall is likely when the patient exits the patient support apparatus 14 unattended. For example, the second set of factors 1104 can include data such as time spent in the bed, sleep deprivation, medical conditions, medications administered to the patient, fall history, falls risk index, gait, vital signs (e.g., blood pressure), and the like.

A third set of factors 1106 can be used to predict patient injury and severity when the patient falls after exiting the patient support apparatus 14 unattended. As an illustrative example, the third set of factors 1106 can include data such as medical condition, age, medications administered to the patient, and the like.

The first, second, and third sets of factors 1102, 1104, and 1106 are weighted, and then combined together to generate a combined score. In some embodiments, the combined score is generated by the data evaluation engine 306 of the system 300 (see FIG. 3). In some embodiments, the data evaluation engine 306 uses machine learning and one or more models from the model building engine 304 to generate the combined scores. Also, the combined scores may be customizable according to the needs of the care facility.

The combined scores are then used to generate classifiers 1108. In some embodiments, the classifier selection engine 308 generates the classifiers 1108 based on the combined scores generated by the data evaluation engine 306. In some embodiments, the classifiers 1108 range from low level classifiers 1108c, to moderate level classifiers 1108b, and to high level classifiers 1108a. Additional levels of classifiers are contemplated to obtain a higher granularity and predictive accuracy in the system 1100.

In certain embodiments, the classifiers 1108 are used to adjust the sensitivity level for the detection algorithms and models from the model building engine 304. For example, high level classifiers 1108a (i.e., ones that indicate increased fall and injury risk), can be used by the detection algorithms and models to bias the classification of uncategorized motion profiles 500 towards exit motions 504.

In some embodiments, the high level classifiers 1108a can result in caregivers setting heightened security measures and increasing alarm sensitivity. For example, the high level classifiers 1108a can result in the caregivers setting fixed exit boundaries on the patient support apparatus 14 such that when a body part of the patient crosses at least one of those boundaries, an alert is automatically generated. Other measures can also be taken to adjust the sensitivity level for the models and detection algorithms for higher risk patients.

The classifiers 1108 are also used to adjust the type of notification or alert generated by the system 1100. Low level classifiers 1108c generate low priority notifications 1110 such as a voice command 1110a directly to the patient to remain in bed and placing a nurse call. A recorded voice prompt 1110b from a loved one of the patient can be sent to the patient. Additional example of low priority notifications 1110 include a status update 1110c on a status board, a visual projection 1110d from the bed, a dome light 1110e, and the like.

High level classifiers 1108a generate high priority alerts 1112 that are sent directly to the caregiver, doctor, or loved one for immediate response. For example, a high priority alert 1112 can be sent directly to a mobile device carried by the caregiver, doctor, or loved one. The system 1100 allows a caregiver to prioritize their workflow given the urgency of the notification or alert generated by the system 1100. In some embodiments, the notifications and alerts are produced by the alert generation engine 310, as described above.

Advantageously, the system 1100 may utilize machine learning techniques to optimize the selection between multiple possible response priorities, and improve the warning time before a patient exits a bed, while reducing false alarms and nuisance calls.

Figure 12:
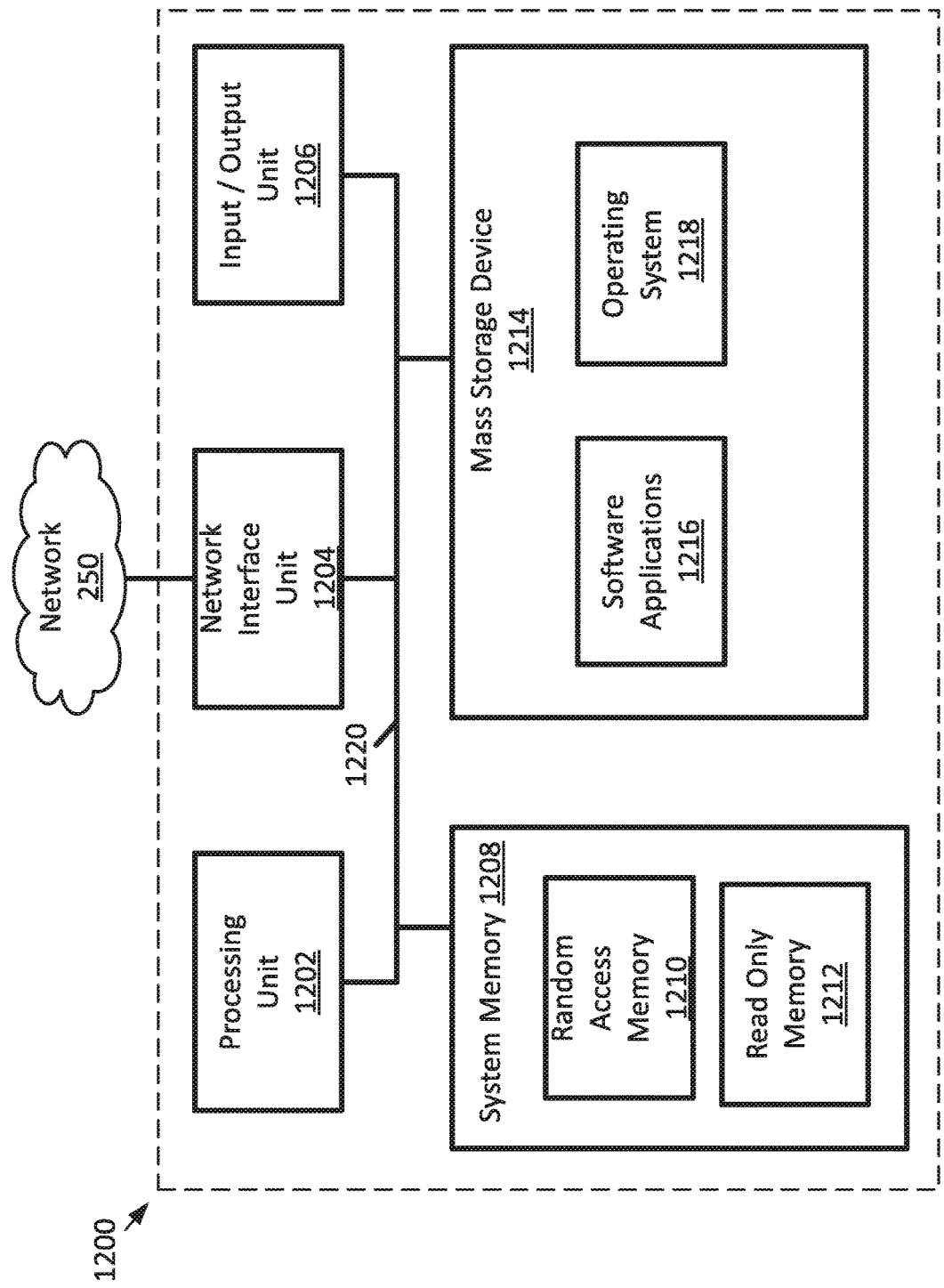
FIG. 12 illustrates example physical components of a computing device.

FIG. 12 illustrates an exemplary architecture of a computing device 1200 which can be used to implement aspects of the present disclosure, such as the functions of the system 300 described above. The computing device 1200 includes a processing unit 1202, a system memory 1208, and a system bus 1220 that couples the system memory 1208 to the processing unit 1202. The processing unit 1202 is an example of a processing device such as a central processing unit (CPU). The system memory 1208 includes a random-access memory ("RAM") 1210 and a read-only memory ("ROM") 1212. A basic input/output logic containing the basic routines that help to transfer information between elements within the computing device 1200, such as during startup, is stored in the ROM 1212.

The computing device 1200 can also include a mass storage device 1214 that is able to store software instructions and data. The mass storage device 1214 is connected to the processing unit 1202 through a mass storage controller (not shown) connected to the system bus 1220. The mass storage device 1214 and its associated computer-readable data storage media provide non-volatile, non-transitory storage for the computing device 1200.

Although the description of computer-readable data storage media contained herein refers to a mass storage device, it should be appreciated by those skilled in the art that computer-readable data storage media can be any available non-transitory, physical device or article of manufacture from which the device can read data and/or instructions. The mass storage device 1214 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The computing device 1200 may operate in a networked environment using logical connections to remote network devices through the network 250, such as a local network, the Internet, or another type of network. The device connects to the network 250 through a network interface unit 1204 connected to the system bus 1220. The network interface unit 1204 may also be utilized to connect to other types of networks and remote computing systems.

The computing device 1200 can also include an input/output controller 1206 for receiving and processing input from a number of input devices. Similarly, the input/output controller 1206 may provide output to a number of output devices.

The mass storage device 1214 and the RAM 1210 can store software instructions and data. The software instructions can include an operating system 1218 suitable for controlling the operation of the device. The mass storage device 1214 and/or the RAM 1210 also store software instructions 1216, that when executed by the processing unit 1202, cause the device to provide the functionality of the device discussed in this document.

The various embodiments described above are provided by way of illustration only and should not be construed to be limiting in any way. Various modifications can be made to the embodiments described above without departing from the true spirit and scope of the disclosure.

What is claimed is:

1. An exit prediction system, comprising:
   a bed including:
   a mattress;
   load cells positioned under the mattress of the bed; and
   a control system included on the bed, the control system including:
   at least one processor; and
   a memory storing instructions which, when executed by the at least one processor, cause the system to:
   receive movement data from the load cells;
   divide the movement data into segments of time;
   extract features from each segment of the segments of time;
   determine a pattern of movement from the extracted features;
   generate a patient exit score based on the determined pattern of movement changing according to a predetermined exit pattern; and
   trigger an alert when the patient exit score exceeds a threshold, wherein the alert is generated on the bed based on the patient exit score.

2. The system of claim 1, wherein the memory stores further instructions which, when executed by the at least one processor, cause the system to:
   generate low, moderate, or high alerts based on the patient exit score.

3. The system of claim 2, wherein the low, moderate, or high alerts are customizable based on factors related to patient fall and injury likelihood when exiting the bed unattended.

4. The system of claim 1, wherein the pattern of movement is configured to be evaluated by a bed exit prediction model built by machine learning, deep learning, or artificial intelligence.

5. The system of claim 4, wherein the bed exit prediction model is built using motion profiles that are pre-categorized as non-exit motions or exit motions.

6. The system of claim 5, wherein the bed exit prediction model is calibrated based on multiple speed classifiers for various patient speeds.

7. The system of claim 1, wherein the extracted features from each segment of time include a percentage change in load detected by the load cells in the bed.

8. The system of claim 7, wherein the memory stores further instructions which, when executed by the at least one processor, cause the system to:
   assign output classes to each segment of the segments of time, each output class of the output classes indicating a decision corresponding to an exit motion type or a non-exit motion type.

9. The system of claim 8, wherein the memory stores further instructions which, when executed by the at least one processor, cause the system to:
   classify the pattern of movement as a non-exit pattern of movement or an exit pattern of movement based on the output classes over time.

10. The system of claim 1, wherein the system is part of a centralized caregiver call system that generates alerts based on the patient exit score.

11. A method of predicting a patient exit from a bed, the method comprising:
- receiving motion profiles, the motion profiles being detected by a plurality of load cells positioned under a mattress of the bed;
- pre-categorizing the motion profiles as non-exit motion or exit motion;
- extracting features from the pre-categorized motion profiles;
- generating a bed exit prediction model using the extracted features;
- predicting the patient exit from the bed using the model by generating a patient exit score based on a pattern of movement changing according to an exit pattern identified by the model; and
- triggering an alert when the patient exit score exceeds a threshold, wherein the alert is generated on the bed based on the patient exit score.

12. The method of claim 11, further comprising:
- generating low, moderate, or high alerts based on the patient exit score.

13. The method of claim 12, further comprising:
- customizing the low, moderate, or high alerts based on additional factors related to patient fall and injury likelihood when a patient exits the bed unattended.

14. The method of claim 11, wherein the bed exit prediction model identifies the exit pattern from the extracted features using machine learning, deep learning, or artificial intelligence.

15. The method of claim 14, wherein the exit pattern is identified by dividing the pre-categorized motion profiles into segments of time, and analyzing a row of features for each segment of the segments of time.

16. The method of claim 15, wherein predicting the patient exit from the bed includes assigning output classes to the segments of time within a motion profile detected from the bed, each output class of the output classes indicating a decision corresponding to an exit motion type or a non-exit motion type.

17. A non-transitory computer readable storage media, including computer readable instructions which when read and executed by a computing device, cause the computing device to:
- receive motion profiles, the motion profiles being detected by a plurality of load cells positioned under a mattress of a bed;
- pre-categorize the motion profiles as non-exit motion or exit motion;
- extract features from the pre-categorized motion profiles;
- generate an exit prediction model using the extracted features; and
- predict a patient exit from the bed using the exit prediction model by generating a patient exit score based on a pattern of movement changing according to an exit pattern identified by the exit prediction model; and
- trigger an alert when the patient exit score exceeds a threshold, wherein the alert is generated on the bed based on the patient exit score.

18. The non-transitory computer readable storage media of claim 17, further comprising computer readable instructions which when read and executed by the computing device, cause the computing device to:
- generate low, moderate, or high alerts based on the patient exit score.

19. The non-transitory computer readable storage media of claim 18, further comprising computer readable instructions which when read and executed by the computing device, cause the computing device to:
- customize the low, moderate, or high alerts based on additional factors related to patient fall and injury likelihood when a patient exits the bed unattended.

20. The non-transitory computer readable storage media of claim 17, wherein to predict the patient exit from the bed includes to assign output classes to segments of time within a motion profile detected from the bed, with each output class of the output classes indicating a decision corresponding to an exit motion type or a non-exit motion type.

* * * * *